(12) United States Patent
Stevens et al.

(10) Patent No.: US 12,059,540 B2
(45) Date of Patent: Aug. 13, 2024

(54) RIGHT VENTRICLE-PULMONARY ARTERY/LEFT VENTRICLE-AORTA CONDUIT

(71) Applicant: Drexel University, Philadelphia, PA (US)

(72) Inventors: Randy Michael Stevens, Merion Station, PA (US); Achintya Moulick, Margate, NJ (US); Vicki Mahan, North Wales, PA (US); Amy L. Throckmorton, Cherry Hill, NJ (US)

(73) Assignee: Drexel University, Philadelphia, PA (US)

( * ) Notice: Subject to any disclaimer, the term of this patent is extended or adjusted under 35 U.S.C. 154(b) by 922 days.

(21) Appl. No.: 17/019,306

(22) Filed: Sep. 13, 2020

(65) Prior Publication Data

US 2021/0077791 A1    Mar. 18, 2021

Related U.S. Application Data

(60) Provisional application No. 62/899,860, filed on Sep. 13, 2019.

(51) Int. Cl.
*A61M 25/10*    (2013.01)
*A61M 25/00*    (2006.01)

(52) U.S. Cl.
CPC .... *A61M 25/1009* (2013.01); *A61M 25/0023* (2013.01); *A61M 25/1025* (2013.01); *A61M 2025/0025* (2013.01); *A61M 2025/1093* (2013.01); *A61M 2205/02* (2013.01); *A61M 2205/04* (2013.01); *A61M 2210/125* (2013.01)

(58) Field of Classification Search
CPC .. A61M 2025/0025; A61M 2025/1093; A61M 2210/125
See application file for complete search history.

(56) References Cited

U.S. PATENT DOCUMENTS

| | | | |
|---|---|---|---|
| 4,769,031 A | 9/1988 | Mcgough et al. |
| 6,616,675 B1 | 9/2003 | Evard et al. |
| 7,766,811 B2 | 8/2010 | Haverich |
| 8,905,961 B2 | 12/2014 | Braido et al. |
| 9,314,556 B2 | 4/2016 | Tuseth |
| 9,993,306 B2 | 6/2018 | Keast et al. |
| 2004/0153112 A1 | 8/2004 | Nissenbaum et al. |
| 2004/0199177 A1 | 10/2004 | Ducksoo |
| 2005/0165344 A1 | 7/2005 | Dobak |

(Continued)

FOREIGN PATENT DOCUMENTS

WO    WO2019142152    7/2019

OTHER PUBLICATIONS

The Children's Heart Clinic. "Right Ventricle to Pulmonary Artery Conduit (RV-PA)" 2012.

(Continued)

*Primary Examiner* — Tiffany Legette
(74) *Attorney, Agent, or Firm* — Joseph E. Maenner; Maenner & Associates, LLC

(57) ABSTRACT

A right ventricle-pulmonary artery conduit provides a first end having a first disc extending radially therefrom and a second disc, proximate to the first disc. The second disc extends radially from the first end. An expandable lumen section extends between the first disc and the second disc. The conduit also has a second end, distal from the first end.

8 Claims, 14 Drawing Sheets

(56) References Cited

U.S. PATENT DOCUMENTS

| | | | |
|---|---|---|---|
| 2007/0299499 A1* | 12/2007 | Hartley | A61F 2/966 623/1.11 |
| 2014/0222040 A1 | 8/2014 | Park et al. | |
| 2015/0258260 A1* | 9/2015 | Tuseth | A61M 60/861 600/16 |
| 2017/0071676 A1* | 3/2017 | Keast | A61B 18/02 |
| 2017/0071722 A1 | 3/2017 | Raifee et al. | |
| 2017/0224323 A1* | 8/2017 | Rowe | A61B 17/0057 |
| 2019/0231510 A1 | 8/2019 | Rafiee et al. | |

OTHER PUBLICATIONS

Rego, Alfredo et al. "Pericardial closure with extracellular matrix scaffold following cardiac surgery associated with a reduction of postoperative complications and 30-day hospital readmissions". Journal of Cardiothoracic Surgery. 2019.

Carag AG. "ASD/PFO occluder with metal free framework" 2020. Not Admitted as Prior Art.

* cited by examiner

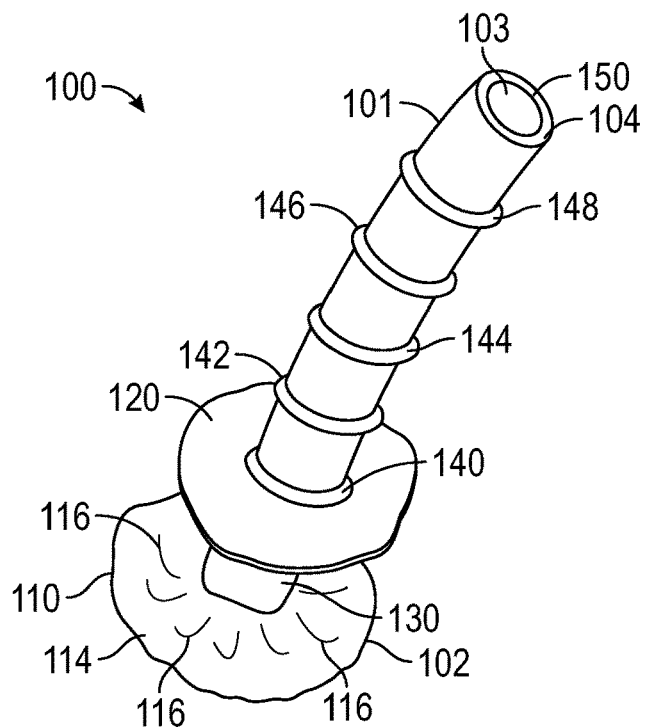
FIG. 3
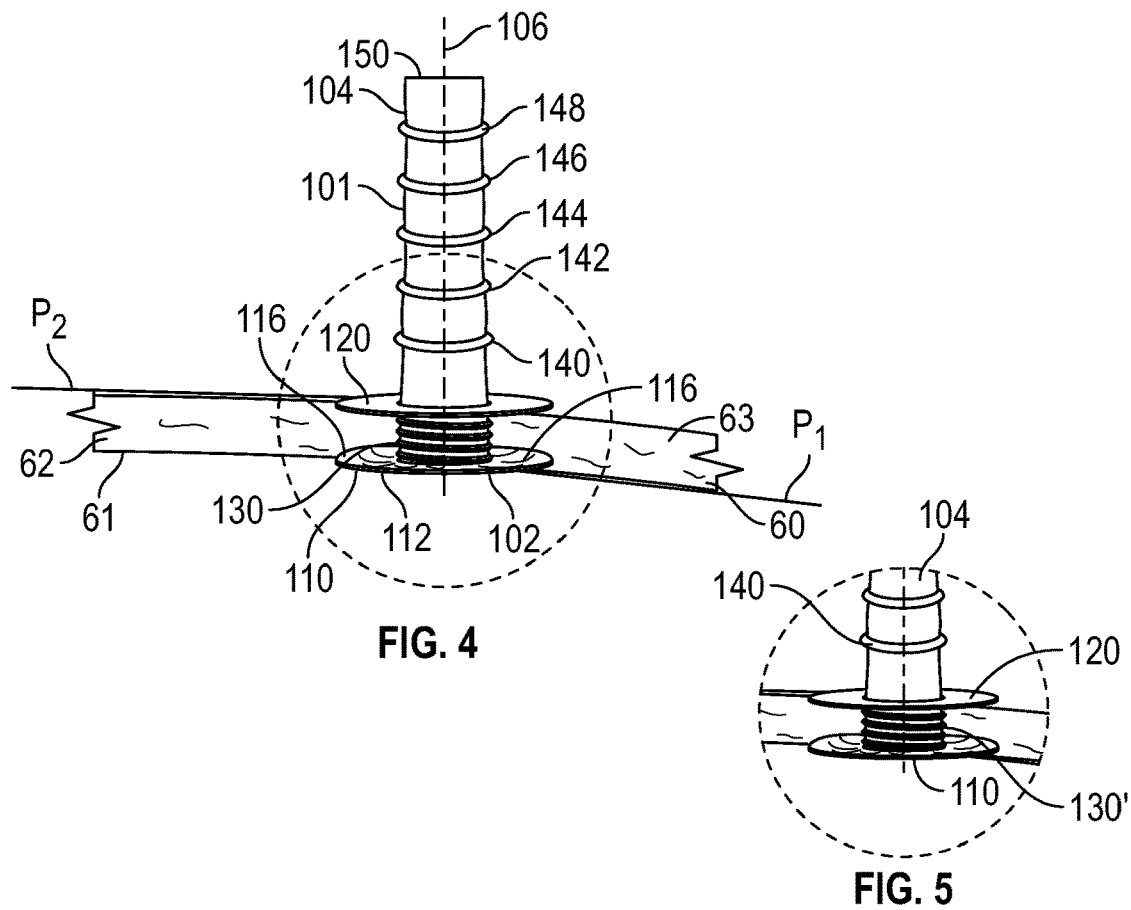
FIG. 4
FIG. 5

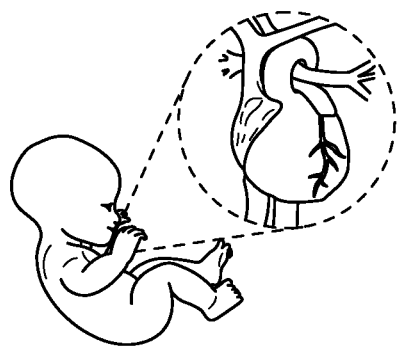
FIG. 13.1
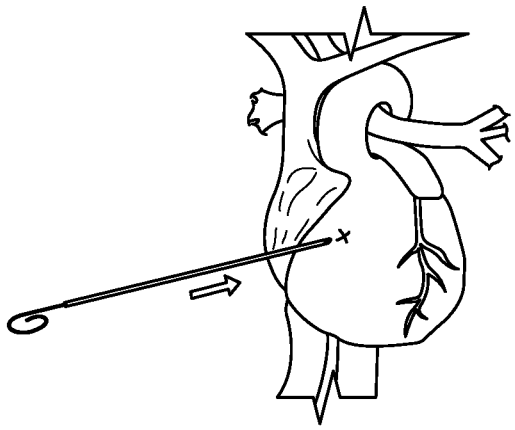
FIG. 13.2
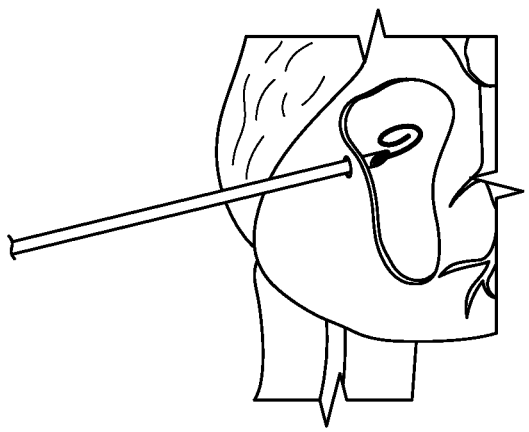
FIG. 13.3
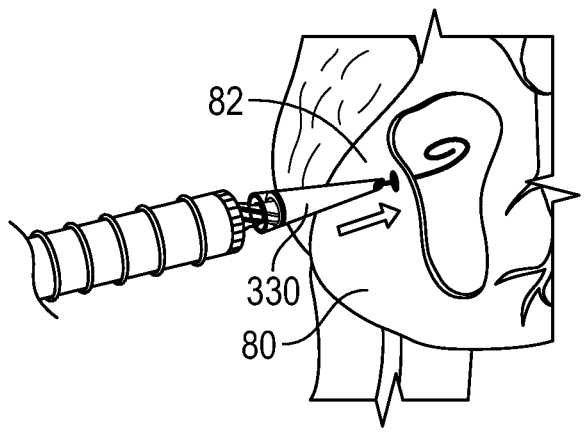
FIG. 13.4
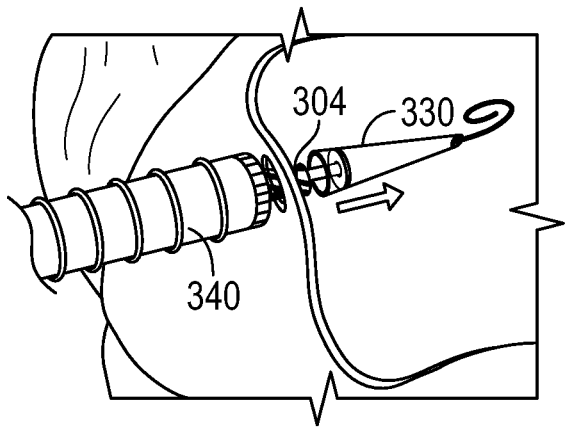
FIG. 13.5
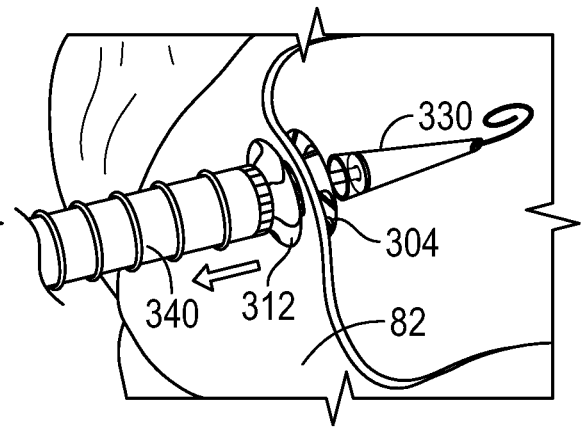
FIG. 13.6

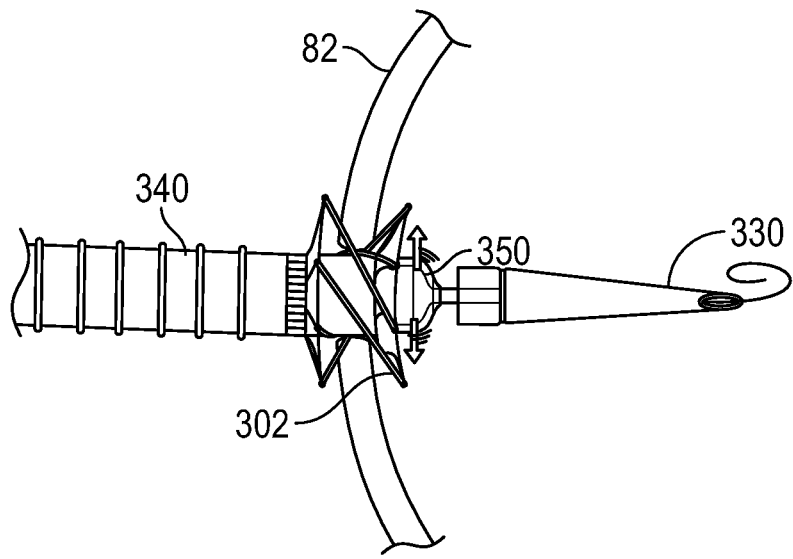
FIG. 13.7
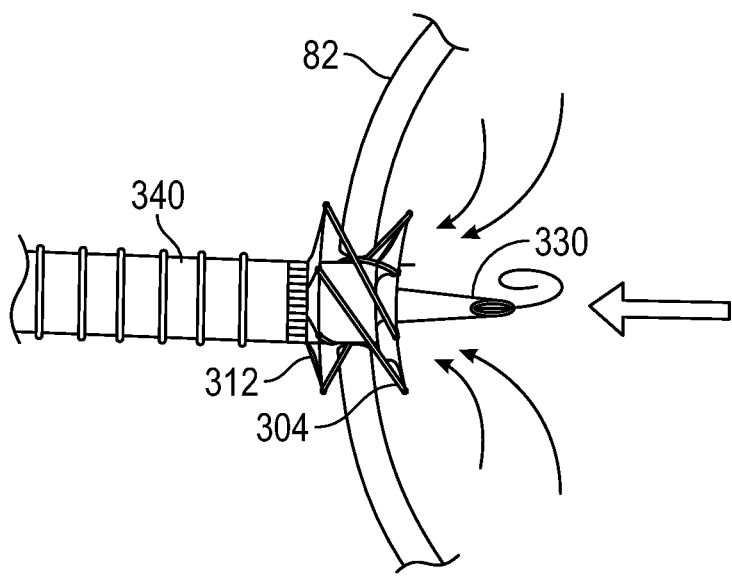
FIG. 13.8

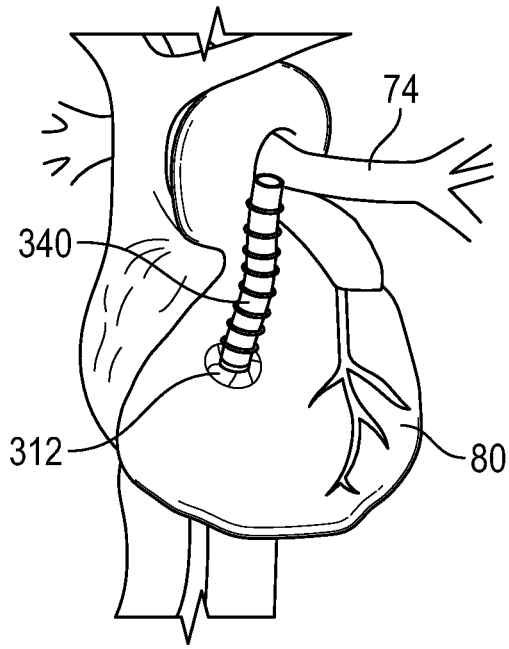
FIG. 13.9
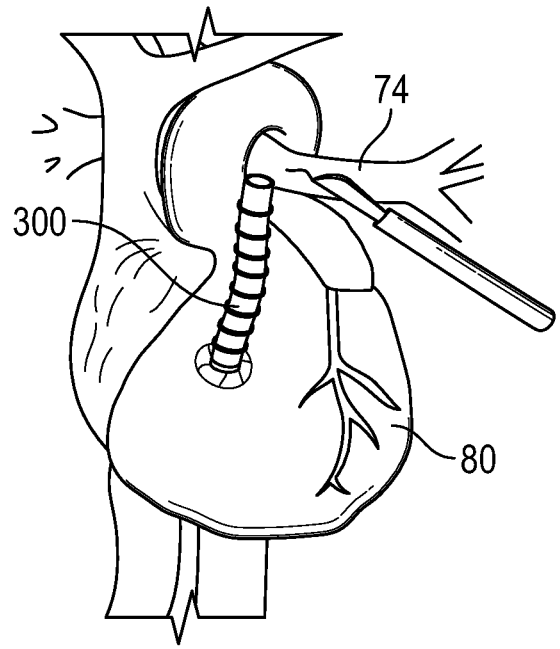
FIG. 13.10
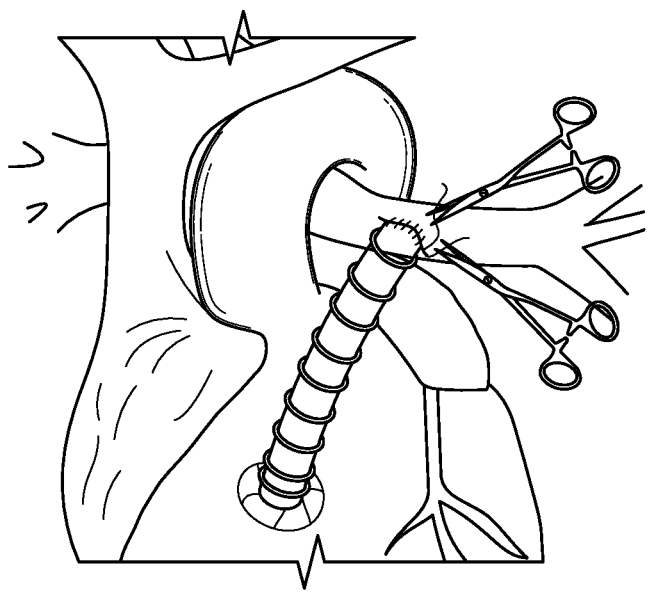
FIG. 13.11
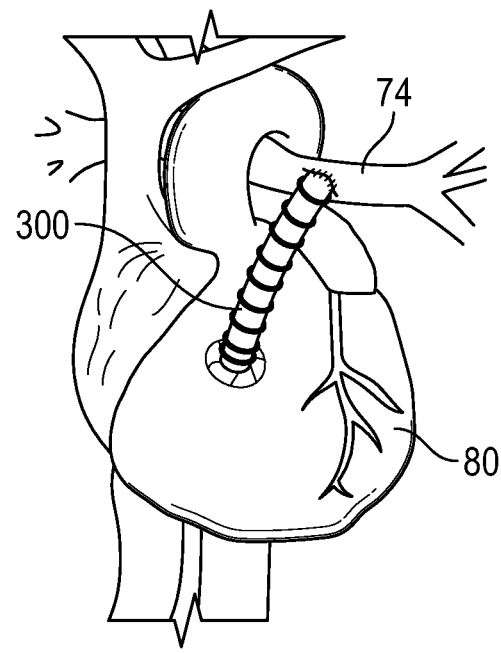
FIG. 13.12

RIGHT VENTRICLE-PULMONARY ARTERY/LEFT VENTRICLE-AORTA CONDUIT

CROSS-REFERENCE TO RELATED APPLICATION

The present application claims the benefit of U.S. Provisional Patent Application Ser. No. 62/899,860, filed on Sep. 13, 2019, which is incorporated herein by reference in its entirety.

BACKGROUND OF THE INVENTION

Field of the Invention

The present invention relates to a right ventricle-pulmonary artery conduit that can be installed in a damaged or defective heart to supply blood to the lungs. Alternatively, the present invention can be used for a variety of left ventricle applications.

Prior Art

Prior art right ventricle-pulmonary artery/left ventricle-aorta (RV-PA) conduits are used as a means to supply blood flow to the lungs. RV-PA conduits can be placed for a variety of heart defects, including tetralogy of Fallot, pulmonary atresia, or pulmonary stenosis. RV-PA conduits are also part of a many complex surgeries for congenital heart disease, including the Ross procedure, Rastelli procedure, or in the Sano modification of the Norwood procedure. RV-PA conduits can be placed to fix a regurgitant (leaky) or stenotic (narrowed) pulmonary valve. RV-PA conduits can also be used to replace an absent right ventricular outflow tract.

Standard insertion requires a median sternotomy (incision through the middle of the chest) through the patient's prior incision, if present. The patient is placed on cardiopulmonary bypass (heart-lung machine). Incisions are made on the pulmonary artery and right ventricle. Prior prosthetic material, if present, is removed. An appropriate sized RV-PA conduit is selected. As shown in FIG. 1, one end of the conduit is sewn onto the incision on the pulmonary artery and the other end is sewn onto the incision on the right ventricle. Typical time to perform the entire surgical procedure can be as long as four (4) hours.

It would be beneficial to provide an RV-PA conduit that does not have to be sewn at both ends, thereby reducing the time to insert the conduit into the patient.

BRIEF SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is a right ventricle-pulmonary artery conduit that provides a first end having a first disc extending radially therefrom and a second disc, proximate to the first disc. The second disc extends radially from the first end. An expandable lumen section extends between the first disc and the second disc. The conduit also has a second end, distal from the first end.

In an alternative embodiment, the present invention provides a right ventricle-pulmonary artery conduit assembly comprising a delivery catheter having a proximal end and a distal end and the conduit described above.

In another alternative embodiment, the present invention provides a right ventricle-pulmonary artery conduit comprising a distal end having an expandable portion. The expandable portion comprises a first disc and a second disc, distal of the first disc. A lumen section provides fluid communication between the first disc and the second disc. A proximal end comprises a conduit body connected to the second disc. The expandable portion is in a collapsed condition in a pre-deployment condition and is in an expanded portion in a post deployment condition, such that the first disc is configured for deployment inside a wall and the second disc is configured for deployment outside the wall.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 3 is a perspective view of the conduit of FIG. 2;

FIG. 4 is a side elevational view of the conduit of FIG. 3;

FIG. 5 is a side elevational view of a coronary lumen section of a right ventricle-pulmonary artery conduit according to an alternative exemplary embodiment of the present invention;

FIG. 13.1 is a schematic showing a heart for which the conduit of FIG. 9 is used in a neo-nate;

FIG. 13.2 is a schematic showing an introducer needle with guide wire ready to access the heart;

FIG. 13.3 is a schematic showing the introducer needle with guide wire accessing the heart;

FIG. 13.4 is a schematic showing a dilator ready to dilate the heart muscle;

FIG. 13.5 is a schematic showing the distal end of the stent structure inserted into the heart;

FIG. 13.6 is a schematic showing the stent disc self-expanding around the heart wall;

FIG. 13.7 is a schematic showing a balloon expanding the inner stent structure;

FIG. 13.8 is a schematic showing the balloon having been removed and the dilator being removed from the heart, with the guide wire intact and arrows depicting blood flow;

FIG. 13.9 is a schematic showing the conduit attached to the ventricle;

FIG. 13.10 is a schematic showing an incision being made in the pulmonary artery;

FIG. 13.11 is a schematic showing the conduit being sutured into the pulmonary artery at the incision;

FIG. 13.12 is a schematic showing the conduit having been sutured to the pulmonary artery;

DETAILED DESCRIPTION

Figure 1:
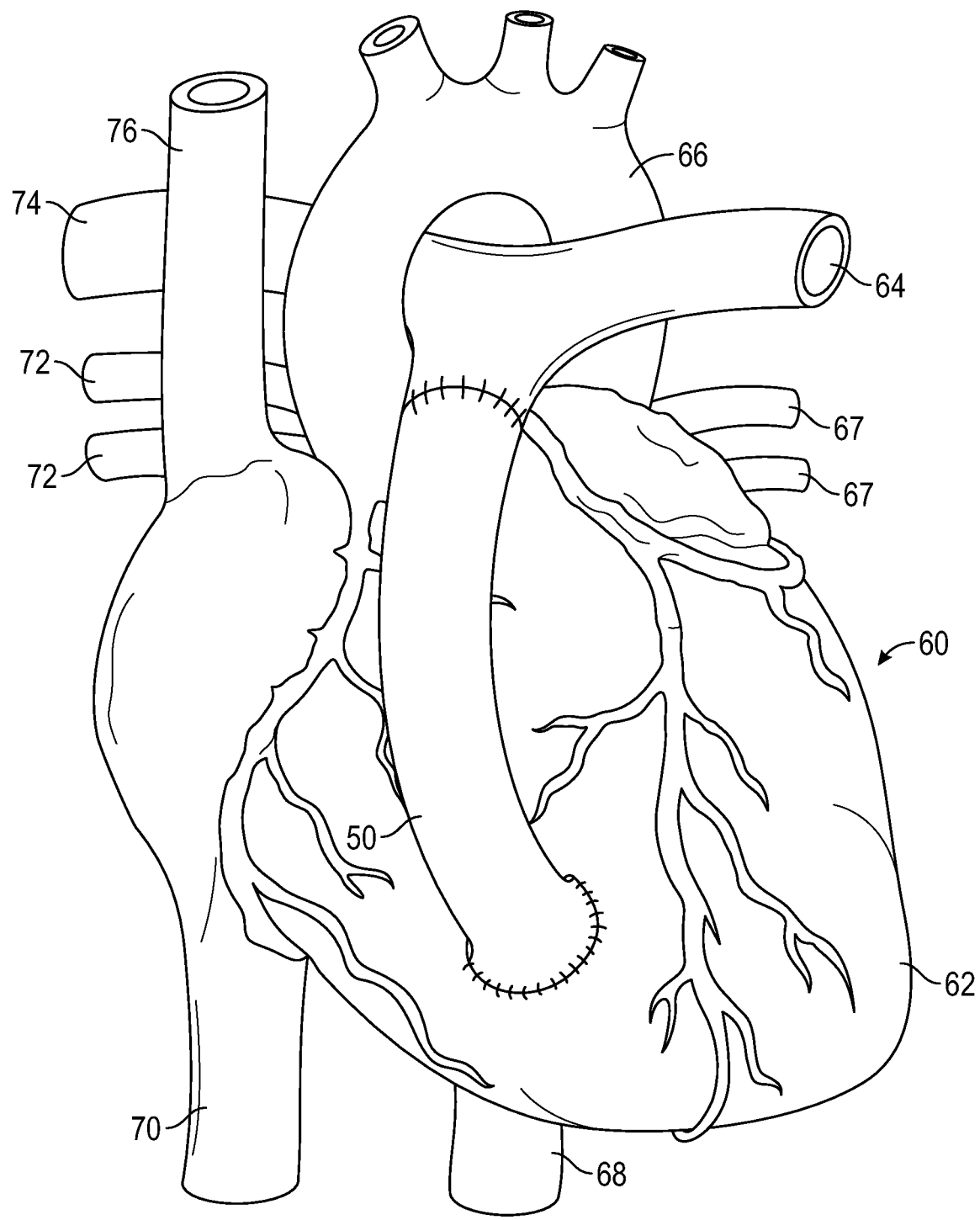
FIG. 1 is a drawing of a defective heart using a prior art right ventricle-pulmonary artery graft.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Referring to FIG. 1, a right ventricle to pulmonary artery (RV-PA) conduit 50 is a means to supply blood flow to the lungs in a damaged or defective heart 60, which can be missing a left ventricle. Conduit 50 can be placed for a variety of heart defects, including Tetralogy of Fallot, pulmonary atresia, or pulmonary stenosis. Conduit 50 is also part of a many complex surgeries for congenital heart disease, including the Ross procedure, Rastelli procedure, or in the Sano modification of the Norwood procedure. Conduit 50 can also be placed to fix a regurgitant (leaky) or stenotic (narrowed) pulmonary valve. Additionally, conduit 50 can also be used to replace an absent right ventricular outflow tract.

Figure 2:
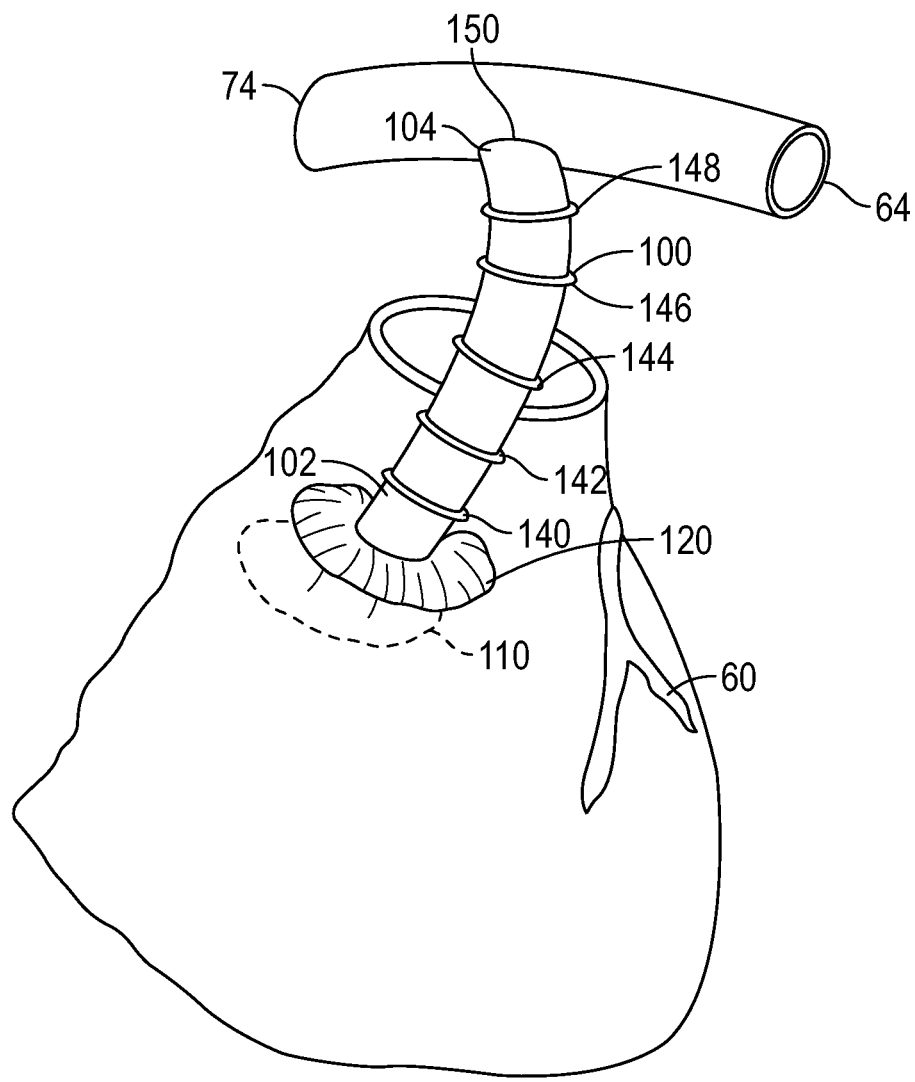
FIG. 2 is a drawing of the defective heart using a right ventricle-pulmonary artery conduit according to an exemplary embodiment of the present invention.

To provide context to FIG. 1, other parts of the heart and associated vasculature are myocardium 62, left pulmonary artery 64, aorta 66, pulmonary veins 67, descending aorta 68, inferior vena cava 70, pulmonary veins 72, right pulmonary artery 74, and superior vena cava 76. Referring to the present invention and FIGS. 2 and 3, a right ventricle-pulmonary artery conduit 100 ("conduit 100") according to an exemplary embodiment can be used for neonates, although those skilled in the art will recognize that larger conduits 100 can be used for older and larger patients. Further, while the present description is directed to the use of conduit 100 in a cardio-pulmonary application, those skilled in the art will recognize that conduit 100 can be used for other applications including, but not limited to, ecmo arterial and venous cannulation as well and other shunt applications.

Conduit 100 is generally an elongated tube with a body 101 having a first, or coronary, end 102 and a second, or pulmonary, end 104. Coronary end 102 is inserted into heart 60, while pulmonary end 104 is inserted into right pulmonary artery 74. In an unattached condition, body 101 can be straight, with a central longitudinal axis 106 extending therethrough. In an exemplary embodiment, body 101 defines a lumen 103 having a diameter of between about 5 mm and about 6 mm, although those skilled in the art will recognize that the diameter of lumen 103 can be other sizes as well.

Coronary end 102 includes a first disc 110 that extends in a first plane P1 transverse to central longitudinal axis 106. First disc 110 can be conformable and can contour to fit the contours of the inside of wall 82. As shown in FIG. 4, plane P1 extends orthogonally from the plane of the paper of FIG. 4. First disc 110 is intended to be inserted through the myocardium of heart 60. First disc 110 has a smooth, planar inner wall 112 that is open to blood flowing through heart 60 and a planar outer wall 114 that engages the endocardium 61 of heart 60. A smooth wall on first disc 110 reduces the likelihood of clots forming on or around first disc 110.

Outer wall 114 includes a plurality of barbed hooks 116 that press into myocardium 62 and help secure coronary end 102 to heart 60. In an exemplary embodiment, hooks 116 are constructed from stainless steel, although those skilled in the art will recognize that other suitable materials can be used. Further, in an exemplary embodiment, 18 hooks 116 can be used, although those skilled in the art will recognize that more or less than 18 hooks 116 can be used. Exemplary hooks can be the same or similar to the hooks used in the PAS-PRT device manufactured by Cardica, Inc. of Redwood City, California.

A second disc 120 that extends in a second plane P2 transverse to central longitudinal axis 106 and parallel to first plane P1. Second disc 120 is intended to remain outside the myocardium 62 of heart 60. Second disc 110 has a smooth, planar outer wall 122 that is closer to pulmonary end 104 and a planar inner wall 124 that engages the epicardium 63 of heart 60. A smooth wall on second disc 120 reduces the likelihood of clots forming on or around second disc 120.

An expandable lumen section 130 extends between first disc 110 and second disc 120. After insertion of coronary end 102 into heart 60, lumen section 130 extends the width of myocardium 62. Lumen section 130 can have an accordion shape that has a length of about 23 mm in an expanded state and about 5-10 mm in a compressed state, depending on the indication. For example, the size range can be between about 5 mm and about 6 mm in hypoplastic left heart syndrome; between about 10 mm and about 20 mm in an adult aorta for a ventricular assist device; or between about 10 mm and about 30 mm in adult Tetratology of Fallot.

Alternatively, as shown in FIG. 5, a lumen section 130' can have an expandable helical structure. With either of lumen section 130 or 130', second disc 120 can be compressed toward first disc 110 after first disc 110 is inserted through myocardium 62 to secure coronary end 102 to heart 60.

Pulmonary end 104 extends from second disc 120, away from expandable lumen section 130. In an exemplary embodiment, pulmonary end 104 can be between about 5 mm and about 7.5 mm long, although those skilled in the art will recognize that pulmonary end 104 can be other lengths. Additionally, pulmonary end 104 can be cut to length prior to insertion, depending on the length need for a particular patient.

Pulmonary end 104 includes a plurality of external support ribs 140-148 that extend circumferentially around the exterior surface of body 101. While five ribs 140-148 are shown, those skilled in the art will recognize that more or less than five ribs 140-148 can be used. In an exemplary embodiment, ribs 140-148 are constructed from nitinol, stainless steel, carbon graphene, or other suitable material. Nitinol is self-expanding when exposed to temperature such as body heat, so pulmonary end 104 can be compressed toward longitudinal axis 106 during implantation of conduit 100. Stainless steel is not self-expanding, and would require an external means of expansion, such as an inflation balloon, in order to expand stainless steel rings. A free end 150 of pulmonary end 104 is inserted into and sutured to right pulmonary artery 74.

Conduit 100 can be constructed from several different materials, depending on the surgical plan and patient's anatomy. Conduit 100 can be constructed from Gore-Tex® (Gore), homograft (cadaver valved tissue), Contegra® (Medtronic) conduits (valved bovine jugular vein), or Hancock® (Medtronic) conduits (Dacron tube graft containing a porcine valve).

Several different indications for placement of conduit 100 are envisioned, namely, for placement during the Norwood operation using the Sano modification; placing an apical left ventricle to aorta conduit for left ventricle outlet obstruction; placing an attachment to the left ventricle for a transapical aortic or mitral valve placement or repair; placing an attachment to the left ventricle for a transapical congenital valve replacement or repair; and placement for attachment of a ventricular assist device. For other such indications, the installed spacing between first disc 110 and second disc 120 can be varied. For example, for installation into myocardium 62 as discussed above, the spacing can be between about 5 mm and about 10 mm; for installation into aorta 66, the spacing can be between about 1 mm and about 2 mm; and for installation into a left ventricle, the spacing can be between about 10 mm and about 20 mm.

To install conduit 100, during the Norwood operation, the patient already is on cardiopulmonary bypass and cooled as is well known in the cardiac surgical art. The right ventricle outflow tract or conus arteriosus distal to pulmonary valve may have been transected. A needle is inserted into the conus arteriosus or right ventricular outflow tract. A guidewire is passed through the needle and the needle is removed. A dilator is inserted and removed over the guidewire. A predetermined size (3, 4, 5, 6 mm diameter) of conduit 100 is passed into the ventricle. The first disc 110 is deployed such that the first disc 100 is inside of the ventricle. Conduit 100 is inside the catheter. The catheter is removed, exposing the first disc 110 such that first disc 110 is contained within the heart 60. Lumen section 130 is housed within the myocardium 62. The second disc 120 is deployed and just outside of the myocardium 62. The body is 5-7.5 mm in length. The remainder of the conduit 100 is a ringed tubed graft, which is measured to size and cut to fit for connection to the pulmonary artery 74.

Figure 5A:
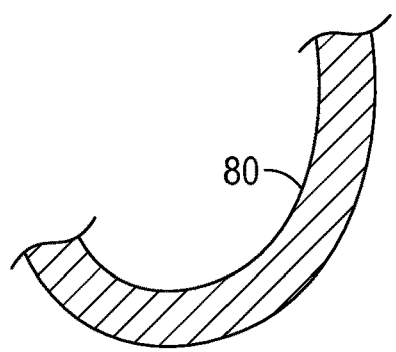
FIG. 5A is a side elevational view, in section of a left or right ventricle.
Figure 5B:
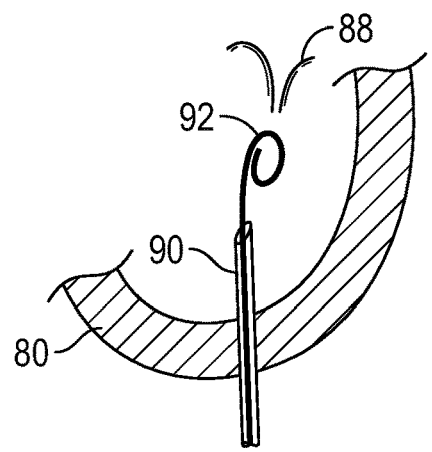
FIG. 5B is a side elevational view, in section, of a needle with guide wire being inserted into the left ventricle of FIG. 5A.

Referring now to FIGS. 5A-5F, for the procedure of placing an apical left ventricle to aorta conduit 200 for left ventricle outlet obstruction, the left ventricle 80 is isolated according to known procedures. As shown in FIG. 5B, a needle 90 is inserted into the ventricle 80 and a guidewire 92 is inserted through the needle 90. The needle 90 is then is removed. A dilator may be used as described above. Hemostasis is controlled with finger pressure. A mitral valve 88 is shown inside heart 80. Conduit 200 can be used to repair mitral valve 88 from below.

Figure 5C:
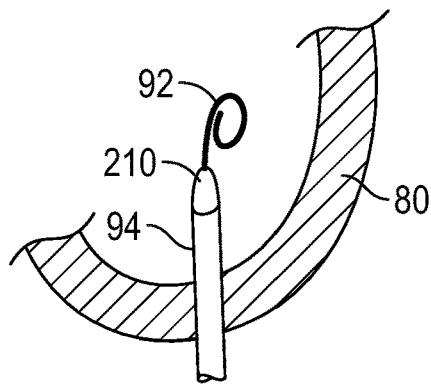
FIG. 5C is a side elevational view, in section of a catheter and introducer being inserted over the guide wire of FIG. 5B.
Figure 5D:
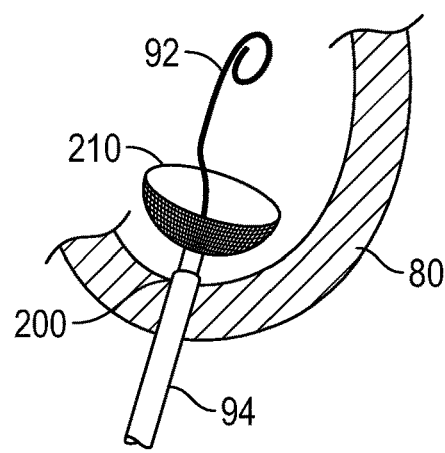
FIG. 5D is a side elevational view, in section, of a conduit according to an alternative exemplary embodiment of the invention, being deployed into the left ventricle.
Figure 5E:
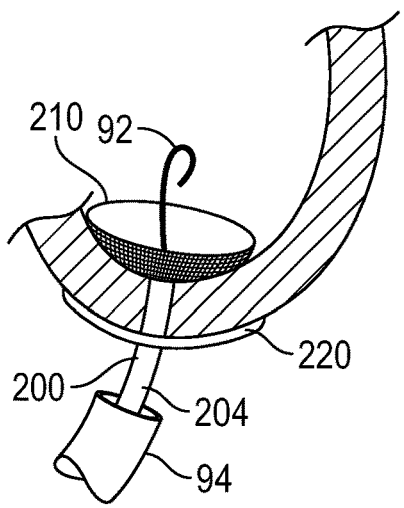
FIG. 5E is a side elevational view, in section of the conduit of FIG. 5D deployed on either side of a wall of the left ventricle.

As shown in FIG. 5C, a catheter 94 is inserted over the wire 92. Conduit 200 is inside the catheter 94. As shown in FIG. 5D, the catheter 94 is slid proximally, exposing the first disc 210. First disc 210 is contained within the left ventricle 80. The catheter 94 is slid farther proximally, as shown in FIG. 5E, exposing a second disc 220, which is deployed outside the left ventricle 80. The pulmonary end 204 attached to the discs 210, 220 is closed off so that no blood escapes. Discs 210, 220 can be curved to generally match the contours of the interior of left ventricle wall 82 and the exterior of wall 82 of left ventricle 80 to provide a seal between the discs 210, 220 and the wall 82.

Figure 5F:
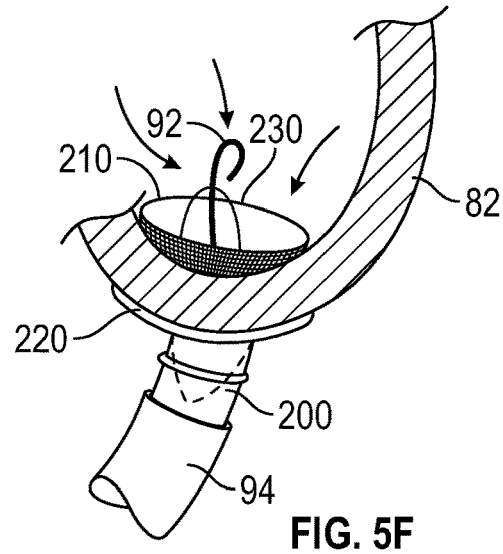
FIG. 5F is a side elevational view, in section, of a balloon being deployed to secure the conduit to the wall to the left ventricle.

As shown in FIG. 5F, a balloon 230 is advanced over guide wire 92 and through conduit 200 to the wall 82 of left ventricle 80. Balloon 230 is expanded to force the wall 202 of conduit between first disc 210 and second disc 220 against the wall 82, sealing conduit 200 to wall 82. The conduit 200 is now usable for transapical valve repair, replacement or intracavitary exploration. Conduit 200 can have different sizes with different inner diameters depending on the specific application for conduit 200. Arrows show the direction of blood flow.

Figure 6:
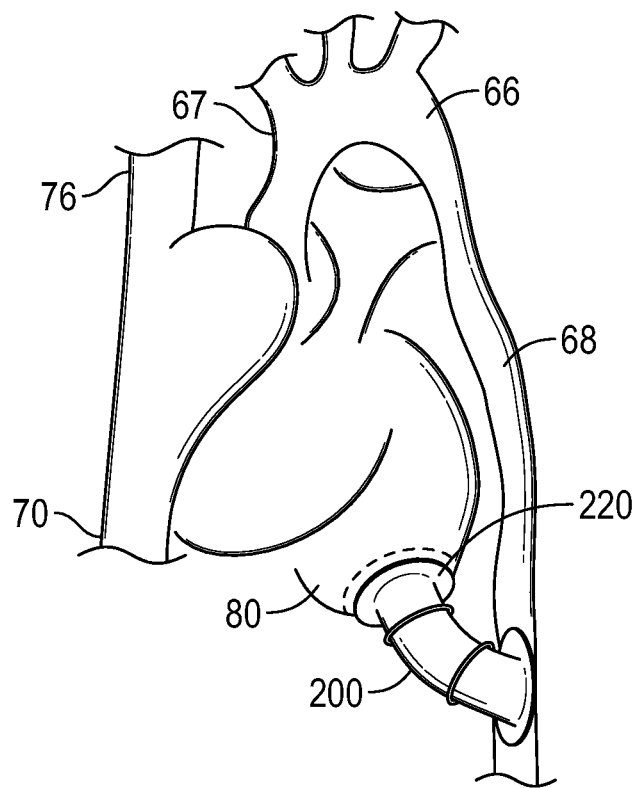
FIG. 6 is a perspective view of the conduit of FIG. 5F attached to a descending aorta.

Once conduit 200 is implanted in left ventricle 80, conduit 200 can be used in several manners. As shown in FIG. 6, conduit 200 can include an inner valve 240 and conduit 200 can be curved to provide for attachment to descending aorta 68 to provide for blood flow from left ventricle 80 directly into descending aorta 68.

Figure 7:
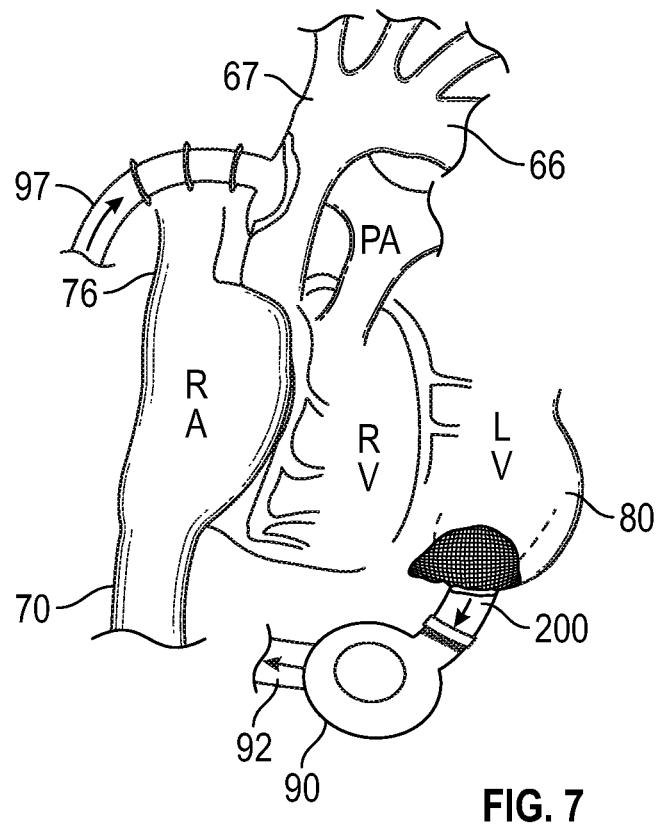
FIG. 7 is a perspective view of the conduit of FIG. 5F attached to an ascending portion of an aorta.

Alternatively, as shown in FIG. 7, conduit 200 can be attached to a ventricular assist device ("VAD") 96 that pumps blood from left ventricle 80 to an ascending portion 67 of aorta 66. VAD 96 has a sufficiently long discharge conduit 98 to extend from VAD 96 to ascending portion 67 of aorta 66.

Figure 8:
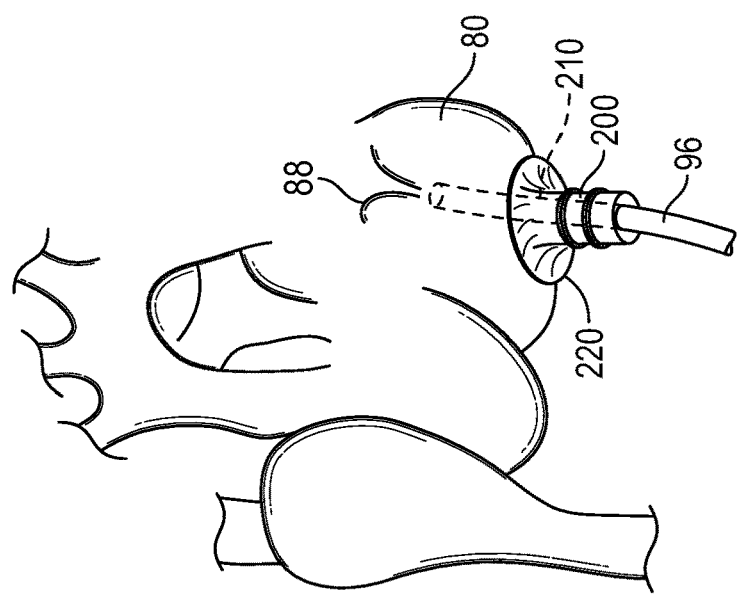
FIG. 8 is a perspective view of the conduit of FIG. 5F providing access into the left ventricle for a catheter.

Still alternatively, as shown in FIG. 8, conduit 200 can be used as an access port to allow for the introduction of a catheter 86 into left ventricle 80, such as, for mitral valve repair or replacement. In this embodiment, the inner diameter of conduit 200 can be sufficiently larger than the outer diameter of catheter 99 to allow for easy manipulation of catheter 99 through wall 82 of left ventricle 80.

The present devices and insertion methods provide multiple benefits over the prior art, namely, saving about 30 minutes of the surgery time; reducing bleeding risk; providing the ability to perform the insertion procedure on a beating heart; and using the incision instead of cutting out a hole in the myocardium preserves myocardium (about 5% of myocardium is removed in the prior art procedure, which is significant).

An alternative embodiment of a conduit 300 according to the present invention is shown in FIGS. 9-13.12. Conduit 300 includes a stent structure 302 that can be deployed on either side of a heart or other organ wall 82. Stent structure 302 includes a distal end 304 formed by a first generally six-sided star having star points constructed from a pliable metal. Connecting portions 308 of each star point are constructed from a rigid metal, as are struts 310 that extend from above each star point to a proximal end 312 formed by a second generally six sided star having star points constructed from the rigid metal.

Figure 10A:
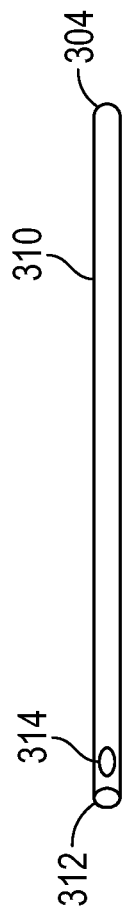
FIG. 10A is a side elevational view of a strut used with the stent assembly of FIG. 10.
Figure 10:
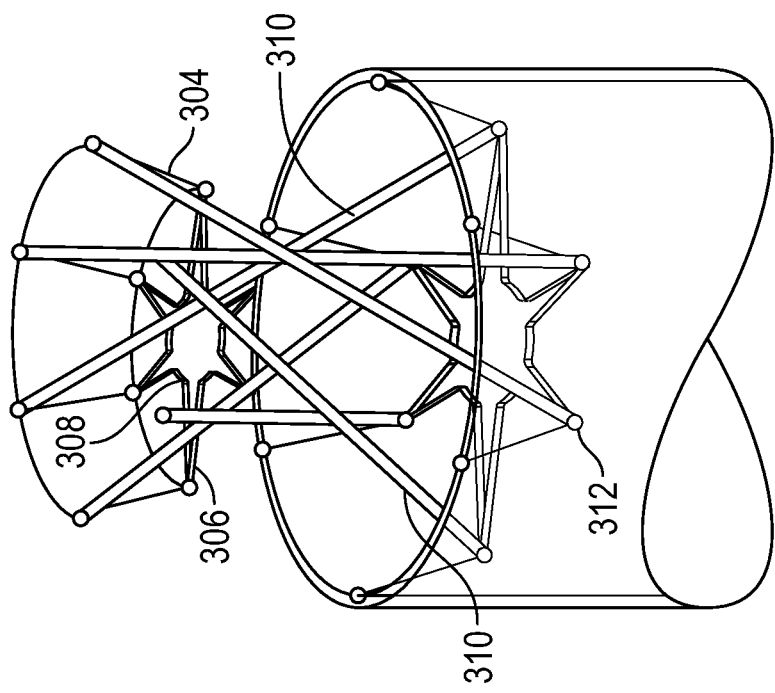
FIG. 10 is a perspective view of a stent structure used with the conduit assembly of FIG. 9, with the covering removed to show skeletal detail.

Optionally, as shown in FIG. 10A, struts 310 can include eyelets 314 proximate to the proximal end to allow for a suture (not shown) to pass through each strut 310.

Figure 11:
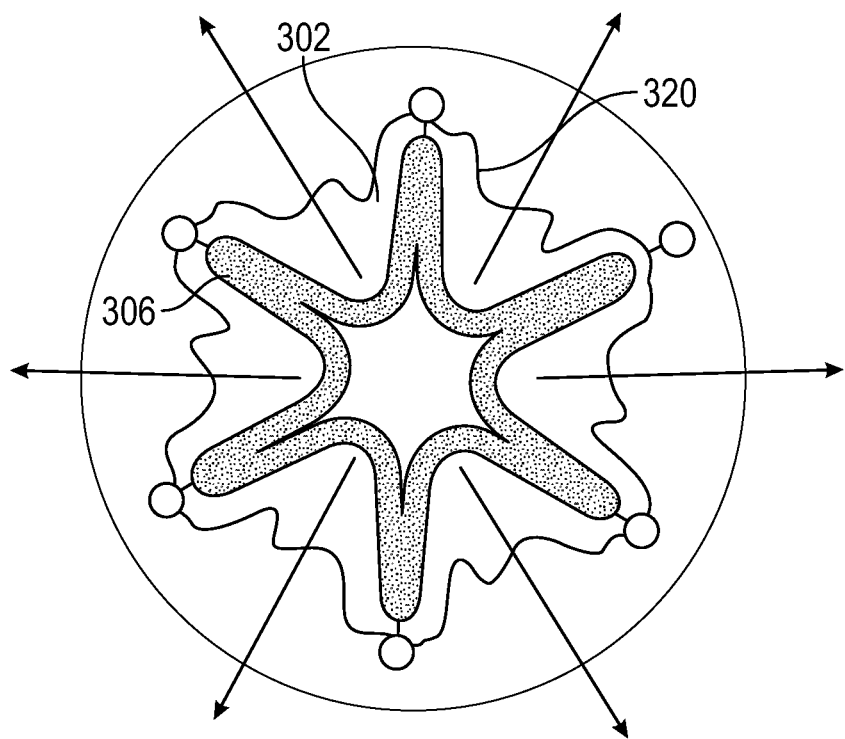
FIG. 11 is a top plan view of the stent structure of FIG. 10 in a compressed configuration.
Figure 12:
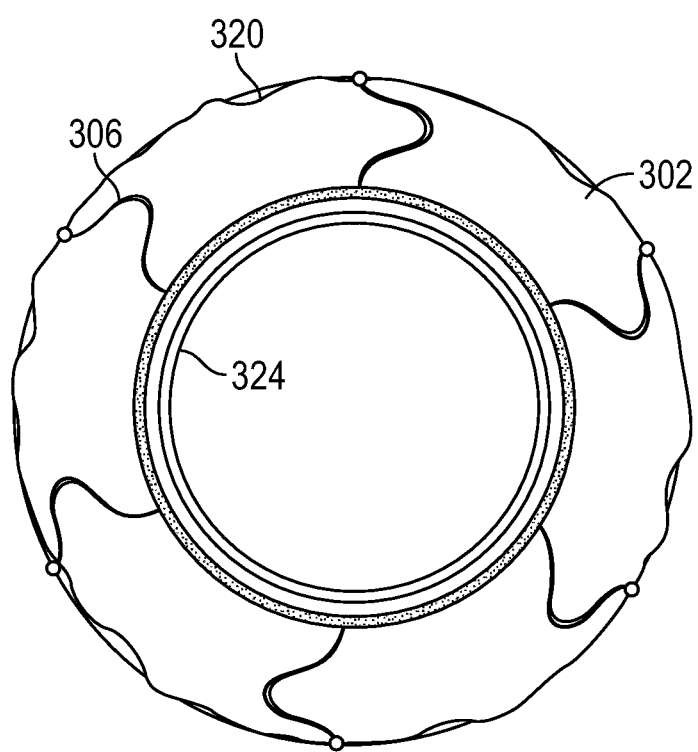
FIG. 12 is a top plan view of the stent structure of FIG. 11 in an expanded configuration.

A first pliable material 320, such as Goretex®, is provided at the distal end 304 and is connected to the distal end of each strut 310 such that, when distal end 304 is expanded, first pliable material 320 expands into a ring. Similarly, a second pliable material 322 is provided at the proximal end 312 and is connected to the proximal end of each strut 310 such that, when proximal end 312 is expanded, second pliable material 322 expands into a ring. Further, a lumen 324 of flexible material extends between distal end 304 and proximal end 312 inside a volume defined by struts 310 such that, when stent structure 302 is expanded, the lumen 324 also expands. FIG. 11 shows stent structure 302 in a compressed position and FIG. 12 shows stent structure 302 in an expanded position.

FIGS. 13.1-13.12 show exemplary steps in deploying conduit 300. In FIG. 13.1, conduit 300 can be used to treat a congenital heart defect such as hypoplastic left heart syndrome. FIGS. 13.2 and 13.3 show the insertion of a guide needle with a guide wire. FIG. 13.4 shows the insertion of conduit 300 with a dilator 330. The dilator 330 dilates heart wall 82 without having to resect any tissue.

FIG. 13.5 shows distal end 304 of stent structure 302 inserted into the heart. FIG. 13.6 shows conduit sleeve 340 pulled proximally, allowing proximal end 312 to expand outside heart wall 82. In FIG. 13.7, a balloon 350 is attached to catheter 301, proximal of dilator 330. Balloon 350 is advanced distally to stent structure 302 and expanded to dilate stent structure 302 and form a seal around the dilated heart wall. Alternatively, stent structure 302 can be self-expanding. While FIG. 13.7 shows conduit sleeve 340 extending generally perpendicularly to heart wall 82, those skilled in the art will recognize that conduit sleeve 340 can be attached to heart wall 82 at other angles. FIG. 13.8 shows dilator 330 and balloon 350 being removed from heart 80 in a proximal direction.

FIG. 13.9 shows conduit 300 having been attached to heart 80. FIG. 13.10 shows an incision being made in pulmonary artery and FIG. 13.11 shows the free end of conduit 300 being sutured into the incision. FIG. 13.12 shows conduit 300 full installed in heart 80 and pulmonary artery 74.

Because one application of conduit 300 is in a neo-natal patient, as the patient grows, the heart will also grow. Heart muscle around the stent structure 302 will also grow and strengthen, but will be unable to expand/contract due to the presence of conduit 300, leading to less effective pumping of blood through the heart.

To overcome this issue, if struts 310 are provided with eyelets 314 as shown in FIG. 10A, with a suture extending through the eyelets, the suture can be grasped through a minimally invasive procedure using just a hook. The suture can be pulled on, resulting in a partial collapse of proximal end 312 of stent structure 302, thereby allowing the heart muscle surrounding stent structure 302 to expand into the space vacated by the collapsed stent structure 302, allowing for possible improved cardiac cell function and providing more heart muscle and more native myocardial function to pump blood.

Figure 9:
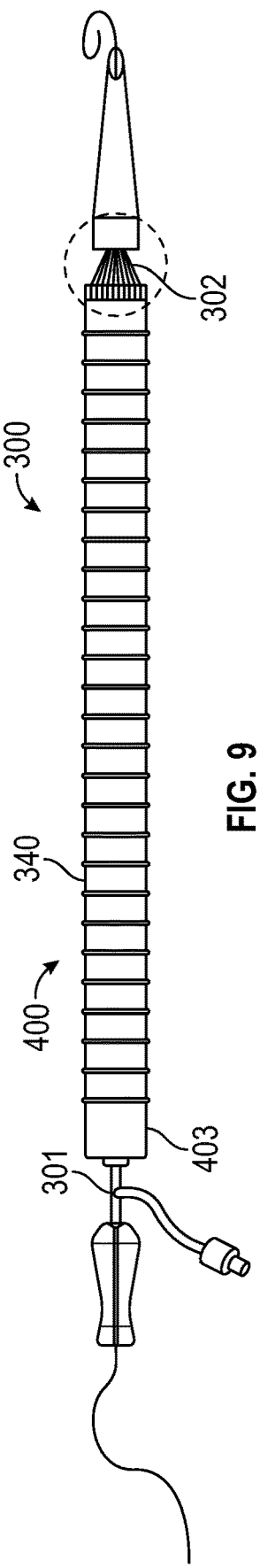
FIG. 9 is a side elevational view of a conduit assembly according to an alternative embodiment of the invention.

Another alternative embodiment of a conduit 400 according to the present invention is shown in FIGS. 14-17 and can be used with an introducer catheter 301, as shown in FIG. 9. Conduit 400 includes a first end 402 that can be deployed on either side of a heart or other organ wall 82 and a second end 403, distal from first end 402.

Figure 14:
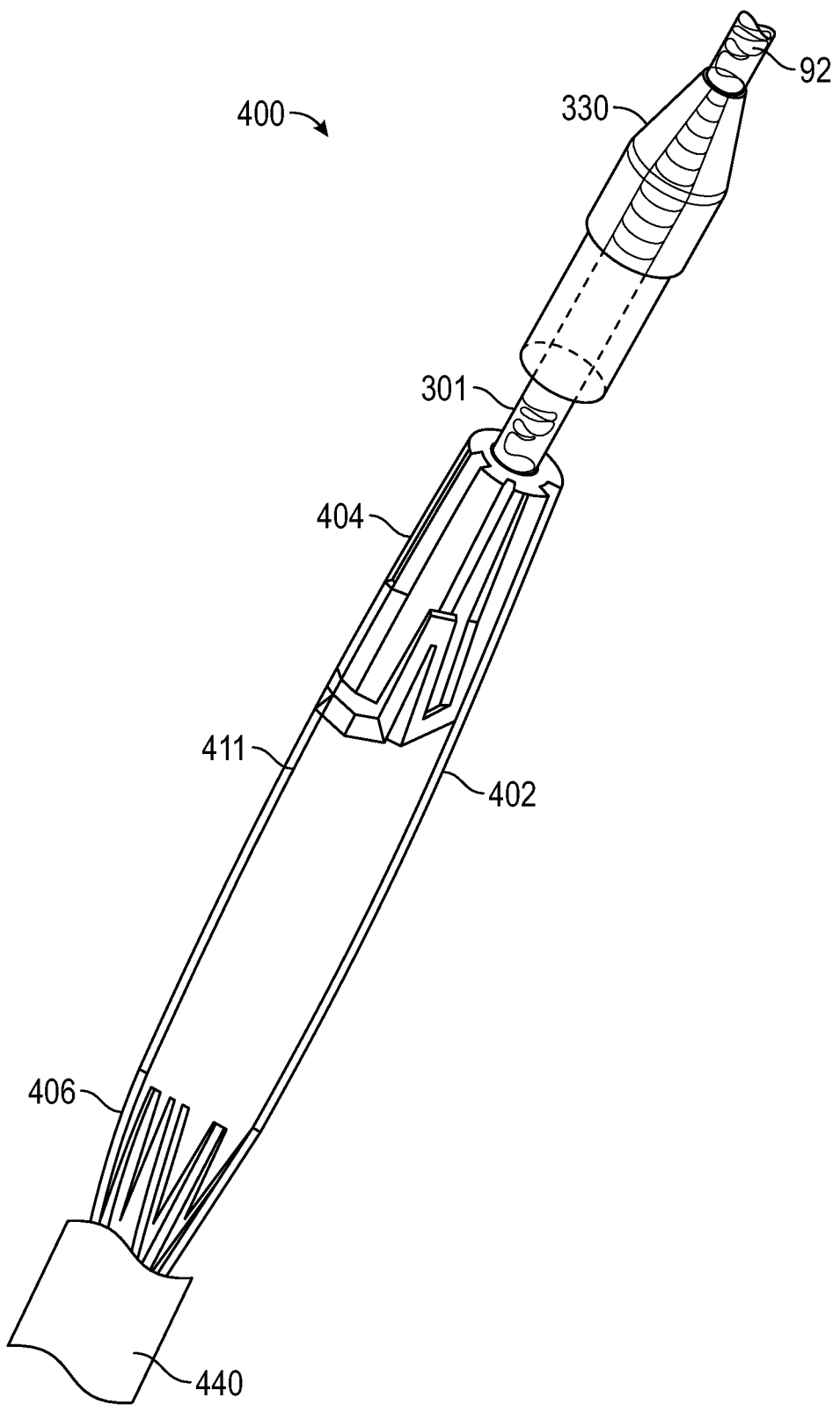
FIG. 14 is a perspective view of a right ventricle-pulmonary artery conduit according to an alternative exemplary embodiment of the present invention.
Figure 15:
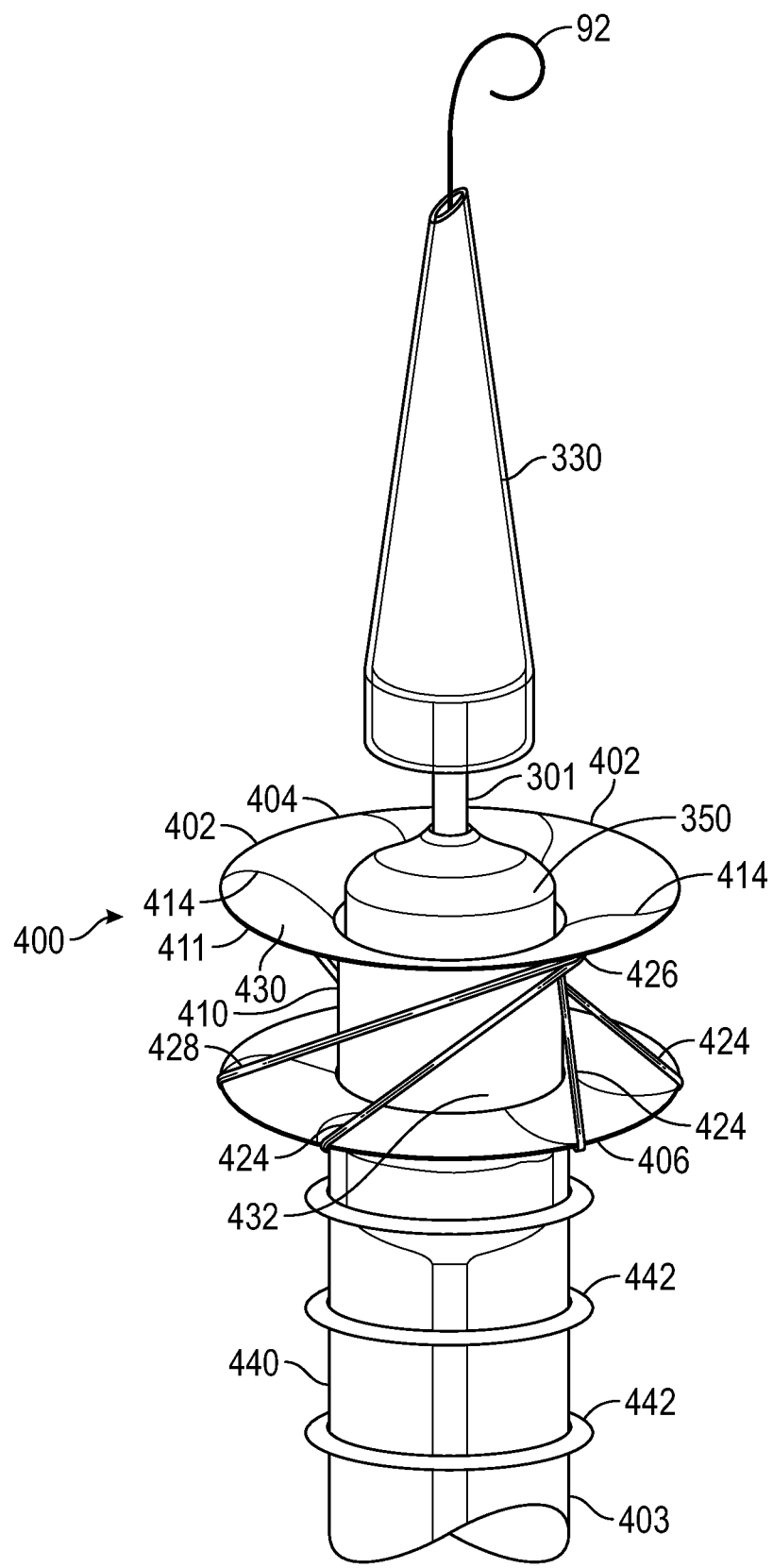
FIG. 15 is a perspective view of a distal end of the conduit of FIG. 14 mounted on an introducer catheter.

Referring to FIGS. 14 and 15, first end 402 includes a collapsible first disc 404 extending radially from first end 402 and a collapsible second disc 406, proximate to the first disc 402, wherein the second disc 406 also extends radially from the first end 402. First disc 404 is configured for insertion on a first side (inside) of heart wall 82 and second disc 406 is configured for insertion on a second side (outside) of heart wall 82. A flexible graft material 411 can be used to cover first and second discs 404, 406 and to form an expandable and collapsible lumen section 410.

Figure 16:
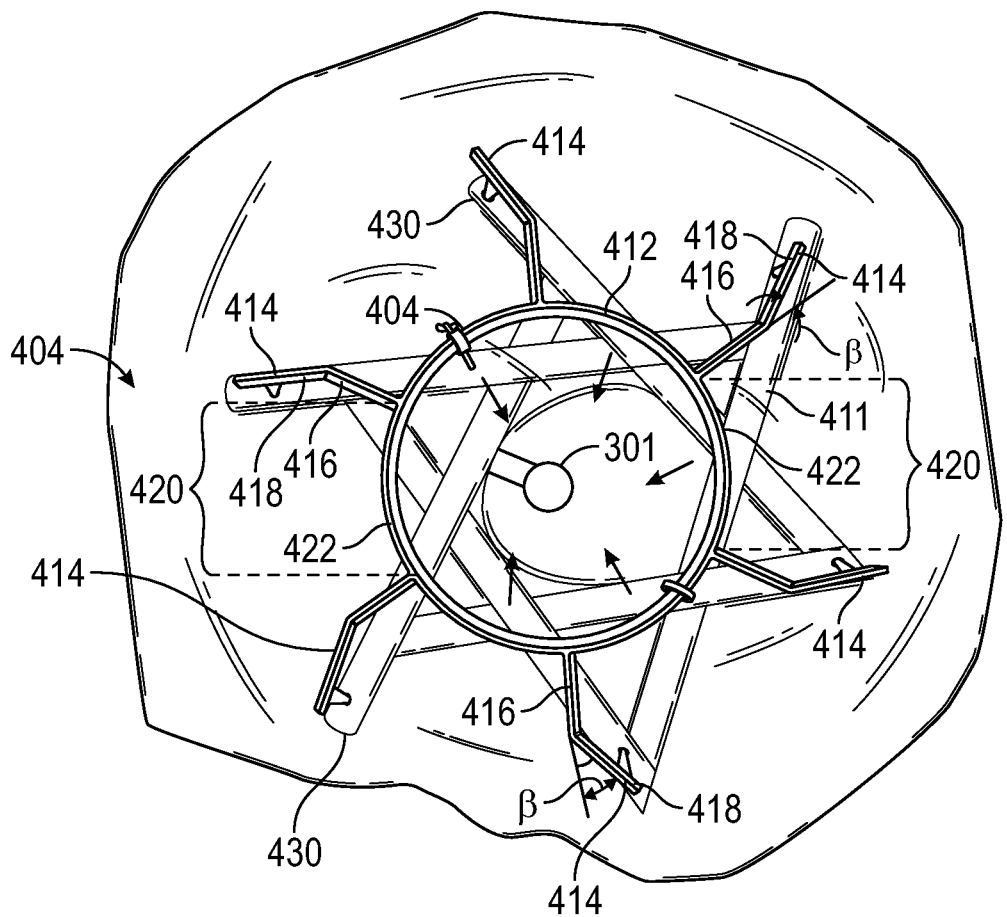
FIG. 16 is a top plan view of the distal end of the conduit of FIG. 14.
Figure 17:
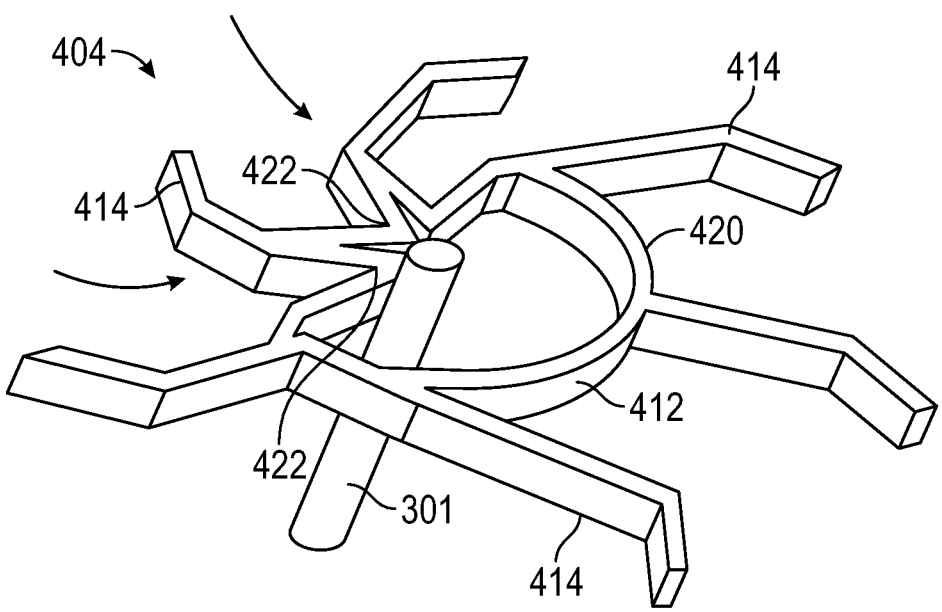
FIG. 17 is a perspective view of a first ring of the distal end of the conduit of FIG. 16, in a partially compressed, undeployed condition.

Referring to FIGS. 16 and 17, first disc 404 comprises a central portion 412 and a plurality of arms 414 extending radially outwardly from the central portion 412. Each arm 414 comprises a connected end 416 and a free end 418, extending at an acute angle β relative to the connected end 416. In an exemplary embodiment, acute angle β is about 30 degrees.

Central portion 412 comprises an arc 420 extending between each adjacent arm 414. Each arc 420 comprises a collapsible joint 422. Additionally, referring back to FIG. 15, first end 402 includes a plurality of struts 424, such that each strut 424 has a first strut end 426 extending from each arm 414 and a second strut end 428 connected to the second disc 406.

Graft material 411 has a first graft end 430 attached to each arm 414 and a second graft end 432 attached to the second disc 406 such that the graft material 411 extends within a perimeter defined by the struts 424 and has a constant diameter between the first disc 404 and the second disc 406.

First disc 404, second disc 406, and struts 424 can be constructed from a shape memory material, such as Nitinol. Alternatively, first disc 404, second disc 406, and struts 424 can be constructed from a bioresorbable material, such as poly lactic acid (PLA) such that first disc 404, second disc 406, and struts 424 ultimately dissolve in the patient's body. In an exemplary embodiment, the flexible graft material 411 can be Goretex®, although those skilled in the art will recognize that other material can be used.

Conduit 400 also includes a conduit body 440 that extends between the second disc 406 and the second end 403 such that second disc 406 is connected to the conduit body 440. Similar to conduit 300, body 440 can include reinforcing support ribs 442.

When conduit 400 is in a compressed position, as shown in FIG. 14, arcs 420 that form central portion 412 are compressed inwardly toward catheter as shown on the left side of FIG. 17. In this position, central portion 412 has a generally star shape. When first end 402 of conduit 400 is released, as shown in FIG. 15, central portion 412 expands and form the ring shown in FIG. 16, It will be further understood that various changes in the details, materials, and arrangements of the parts which have been described and illustrated in order to explain the nature of this invention may be made by those skilled in the art without departing from the scope of the invention as expressed in the following claims.

We claim:

1. A right ventricle-pulmonary artery conduit comprising:
    a distal end having:
        a first disc extending radially therefrom;
        a second disc, proximate to the first disc, wherein the second disc extends radially from the first end; and
        an expandable lumen section extending between the first disc and the second disc;
    a stent structure connecting the first disc and the second disc with each other, the stent structure comprising a plurality of linear struts; and
    a proximal end, distal from the distal end;
    a longitudinal axis extending between the distal end and the proximal end such that the struts extend obliquely relative to the longitudinal axis to support the first disc and the second disc; and
    a conduit attached to the second disc and extending to the proximal end, the conduit having a plurality of reinforcing rings extending radially along a length thereof.

2. The right ventricle-pulmonary artery conduit according to claim 1, wherein the first disc is collapsible.

3. A right ventricle-pulmonary artery conduit assembly comprising:
    a delivery catheter having a proximal end and a distal end; and
    a right ventricle-pulmonary artery conduit removably mounted on the distal end of the catheter, the conduit comprising:
        a first end having:
            a distal disc extending radially therefrom, the distal disc being constructed from a first pliable material;
            a proximal disc, proximate to the distal disc, wherein the proximal disc extends radially from the first end, the proximal disc being constructed from a second pliable material;
            a plurality of linear struts connecting the distal disc to the proximal disc; and
            an expandable lumen section extending between the distal disc and the proximal disc inside a volume defined by the struts; and
        a second end, distal from the first end the second end having a conduit extending away from the second disc, the conduit comprising a plurality of reinforcing rings around n external perimeter thereof.

4. The assembly according to claim 3, further comprising a dilatation balloon fixed to the catheter.

5. The assembly according to claim 4, further comprising a dilator fixed to the catheter such that the balloon is proximal of the dilator.

6. The assembly according to claim 5, wherein the dilator removably engages the lumen section.

7. The assembly according to claim 5, wherein the first disc is collapsible.

8. A right ventricle-pulmonary artery conduit comprising:
    a distal end having an expandable portion, the expandable portion comprising:
        a first disc constructed from a first pliable material;
        a second disc, proximal of the first disc, the second disc constructed from a second pliable material;
        a plurality of straight, linear struts connecting and supporting the first disc and the second disc to each other; and
        a lumen section providing fluid communication between the first disc and the second disc; and
    a proximal end comprising a conduit body connected to and extending proximally from the second disc,
    wherein the expandable portion is in a collapsed condition in a pre-deployment condition and is in an expanded position in a post deployment condition, such that the first disc is configured for deployment inside a wall, the second disc is configured for deployment outside the wall.

* * * * *